US012752107B2

(12) United States Patent
Leonhardt et al.

(10) Patent No.: US 12,752,107 B2
(45) Date of Patent: Oct. 6, 2026

(54) MODULATION OF SIRT

(71) Applicant: Leonhardt Ventures LLC, Mission Viejo, CA (US)

(72) Inventors: Howard J. Leonhardt, Mission Viejo, CA (US); Jorge Genovese, Irvine, CA (US)

(73) Assignee: LEONHARDT VENTURES LLC, Mission Viejo, CA (US)

( * ) Notice: Subject to any disclaimer, the term of this patent is extended or adjusted under 35 U.S.C. 154(b) by 319 days.

(21) Appl. No.: 18/473,921

(22) Filed: Sep. 25, 2023

(65) Prior Publication Data

US 2024/0108886 A1 Apr. 4, 2024

Related U.S. Application Data

(60) Provisional application No. 63/377,664, filed on Sep. 29, 2022.

(51) Int. Cl.

| | |
|---|---|
| ***A61N 1/20*** | (2006.01) |
| ***A61N 1/04*** | (2006.01) |
| ***A61N 1/32*** | (2006.01) |
| ***A61N 1/36*** | (2006.01) |

(52) U.S. Cl.
CPC .......... *A61N 1/205* (2013.01); *A61N 1/0492* (2013.01)

(58) Field of Classification Search
CPC ........ A61N 1/08; A61N 1/36; A61N 1/36002; A61N 1/36003; A61N 1/36014; A61N 1/36017; A61N 1/36021; A61N 1/036025; A61N 1/40
See application file for complete search history.

(56) References Cited

U.S. PATENT DOCUMENTS

2012/0310298 A1* 12/2012 Besio .................. A61B 5/4094 607/45
2013/0079834 A1* 3/2013 Levine .............. A61N 1/36053 607/45

* cited by examiner

*Primary Examiner* — Brian T Gedeon
(74) *Attorney, Agent, or Firm* — TraskBritt

(57) ABSTRACT

Described is a low voltage, pulsed electrical stimulation device for modulating the expression of sirtuin ("SIRT"), a useful protein, by tissues. Also described are methods of enhancing expression of SIRT in cells, particularly a method of stimulating the expression and/or release of SIRT in a cell having a gene encoding SIRT, wherein the method includes applying a bioelectric signal of, within 15%, 50 μA to about 500 μA, 20 pps, at 400 μsec pulse duration to the cell (e.g., directly, indirectly, or wirelessly). In order to downregulate expression of SIRT, the at least one bioelectric signal has a current of at least about 1 mA, as measured at the level of the living cells.

16 Claims, 5 Drawing Sheets

MODULATION OF SIRT

CROSS-REFERENCE TO RELATED APPLICATION

This application claims the benefit under 35 U.S.C. § 119(e) of U.S. Provisional Patent Application Ser. No. 63/377,664, filed Sep. 29, 2022, the contents of the entirety of the disclosure of which are hereby incorporated herein in its entirety by this reference.

TECHNICAL FIELD

The application relates generally to the field of medical devices and associated methods of treatment, and more specifically to methods of treatment involving the precise bioelectrical stimulation of a subject's tissue, optionally augmented with the administration of a composition comprising, among other things, stem cells and nutrients, useful to increase the expression and/or release of sirtuin ("SIRT") to stimulate and treat the subject, the subject's tissue(s), the subject's organ(s), and/or the subject's cells. More specifically, the application relates to a device, programmed to produce bioelectric signals, and associated methods for the controlled expression of secreted SIRT via application of such bioelectric signals.

BACKGROUND

As described by Grabowska et al., "Sirtuins, a promising target in slowing down the ageing process," *Biogerontology,* 2017; 18(4): 447-476, one of the most promising targets for anti-ageing approaches are proteins belonging to the sirtuin family. Sirtuins are known to occur in yeast, bacteria and eukaryotes (including mammals). In humans, the family has seven members (SIRT1-7) that possess either mono-ADP ribosyltransferase or deacetylase activity. Sirtuins are believed to play a key role during cell response to a variety of stresses, such as oxidative or genotoxic stress and are crucial for cell metabolism. It was documented that proper lifestyle including physical activity and diet can influence health span via increasing the level of sirtuins.

Further, as disclosed by Lee et al. (2019), sirtuin is an essential factor that delays cellular senescence and extends the organismal lifespan through the regulation of diverse cellular processes. Suppression of cellular senescence by sirtuin is mainly mediated through delaying the age-related telomere attrition, sustaining genome integrity and promotion of DNA damage repair. In addition, Sirtuin modulates the organismal lifespan by interacting with several lifespan regulating signaling pathways including insulin/IGF-1 signaling pathway, AMP-activated protein kinase, and forkhead box O. Although still controversial, it is suggested that the pro-longevity effect of Sirtuin is dependent with the level of and with the tissue expression of sirtuin. Lee et al., "Sirtuin signaling in cellular senescence and aging," *BMB Rep.* 2019 January; 52(1): 24-34.

SIRT6, the so-called "longevity sirtuin" is a protein that is vital for both normal base excision repair (BER) and double-strand break repair of DNA damage. Xu et al., "SIRT6 rescues the age-related decline in base excision repair in a PARP1-dependent manner," *Cell Cycle,* 2015; 14(2): 269-276. These repairs decline with age but can be boosted with SIRT6.

Sirt6 is a critical anti-aging molecule that regulates various cellular processes associated with aging and protects the heart from developing aging-induced cardiac hypertrophy and fibrosis. Pillai et al., "The nuclear sirtuin SIRT6 protects the heart from developing aging-associated myocyte senescence and cardiac hypertrophy," *Aging* (Albany NY). 2021 May 2; 13(9):12334-12358.

Tian et al. demonstrated that an overexpression of SIRT6 protein leads to extended lifespan and that a deficiency in SIRT6 can cause premature aging. Tian et al., "SIRT6 Is Responsible for More Efficient DNA Double-Strand Break Repair in Long-Lived Species," *Cell* Volume 177, Issue 3, P622-638.E22 (Apr. 18, 2019).

It would be an improvement in the art to have a way to modulate the expression of sirtuins.

BRIEF SUMMARY

Described herein is a bioelectric stimulator particularly configured to modulate (e.g., upregulate or downregulate) the expression and/or release of sirtuin in cellular tissue.

Further described are precise bioelectric signals that upregulate and downregulate cellular expression levels of circulating sirtuin on demand with control.

Particularly described is a bioelectric stimulator comprising an electric signal generator and electrode(s), which electric signal generator is programmed to produce at least one bioelectric signal that stimulates target tissue comprising living cells so as to modulate expression and/or release of sirtuin (SIRT) by the living cells of the target tissue, wherein the bioelectric signal comprises a bioelectric signal having a biphasic pulse at a frequency of, within 15%, 20 Hz, with a pulse width of, within 15%, 400 microseconds (μsec) and has a current of less than 1 milliAmp (mA) as measured at the level of the living cells of the target tissue.

In certain embodiments, the bioelectric signal has a current of less than 575 microAmp (μA), as measured at the level of the living cells of the target tissue, which bioelectric signal upregulates expression of SIRT by the living cells. In certain such embodiments, the bioelectric signal has a current of from about 50 μA to about 500 μA. For example, the bioelectric signal may have a current of 50 μA or 500 μA.

Also described are methods of using such a bioelectric stimulator to stimulate target tissue comprising living cells of a subject to modulate the expression of SIRT by the living cells, the method comprising: administering the bioelectric signal to the living cells via the electrode(s) for from about 5 minutes to about an hour, so as to modulate the expression of SIRT by the living cells. In certain such embodiments, the SIRT modulated comprises sirtuin 1 and/or sirtuin 6.

Also described herein are methods of stimulating living cells so as to modulate expression and/or release of sirtuin (SIRT) by the living cells, the method comprising: applying at least one bioelectric signal having a biphasic pulse at a frequency of, within 15%, 20 Hz, with a pulse width of, within 15%, 400 microseconds (μsec) and having a current of less than 1 mA as measured at the level of the stimulated living cells to stimulate the living cells to modulate the expression of SIRT by the living cells. Preferably, the at least one bioelectric signal is administered to the living cells for from about five (5) minutes to about an hour, so as to modulate the expression of SIRT by the living cells. In order to upregulate expression of SIRT, the at least one bioelectric signal preferably has a current of less than 575 μA (e.g., from about 50 μA to about 500 μA), as measured at the level of the living cells. As used herein, "about" means plus or minus 5%. In order to downregulate expression of SIRT, the at least one bioelectric signal preferably has a current of at least about 1 mA, as measured at the level of the living cells.

Such methods may be used to treat a subject, such as one diagnosed as suffering from heart failure, arthritis, erectile dysfunction, osteopenia, osteoporosis, metabolic stress, metabolic syndrome, spinal cord injury, liver disease or dysfunction, skin disorder(s), hair loss, sexual dysfunction, energy homeostasis, lack of physical activity, diabetes, hypertension, arterial calcification, valve calcification, Alzheimer's disease, dementia, cognitive function, depression, addiction, pre-mature aging related disorder, senescence, aging, muscle atrophy, inflammation, and/or COVID-19 infection. Uses in odontics are also contemplated.

Also described is a method of inhibiting (or downregulating) expression of sirtuin (SIRT) in a subject utilizing a bioelectric stimulator, wherein the bioelectric stimulator comprises an electric signal generator and associated electrode(s), which electric signal generator is programmed to produce at least one bioelectric signal that stimulates target tissue comprising living cells so as to inhibit expression and/or release of sirtuin (SIRT) by the living cells of the target tissue, wherein the bioelectric signal comprises a bioelectric signal having a biphasic pulse at a frequency of, within 15%, 20 Hz, with a pulse width of, within 15%, 400 microseconds (μsec) and has a current of at least 1 mA as measured at the level of the living cells of the target tissue, the method comprising: stimulating the target tissue of the subject. In certain such embodiments, the bioelectric signal has a current of 5 mA. Such methods may be used, for example, to downregulate expression of SIRT in a subject after stimulation, e.g., as described herein or for treating symptoms of Parkinson's disease and certain types of depression.

DETAILED DESCRIPTION

In certain embodiments, described is a low voltage, pulsed electrical stimulation device for modulating expression of sirtuin ("SIRT"), a useful protein, by tissues. Also described are methods of enhancing expression of SIRT in cells, particularly a method of stimulating the expression and/or release of SIRT in a cell having a gene encoding SIRT, wherein the method includes applying a bioelectric signal of from about 1 Hz to about 100 Hz (e.g., 1 Hz, 5 Hz, 10 Hz, 40 Hz, 100 Hz, or 110 Hz) to the cell (e.g., directly, indirectly, or wirelessly). Applications in the treatment of Alzheimer's disease, depression, schizophrenia, and post-traumatic stress disorder are also disclosed.

Figure 1:
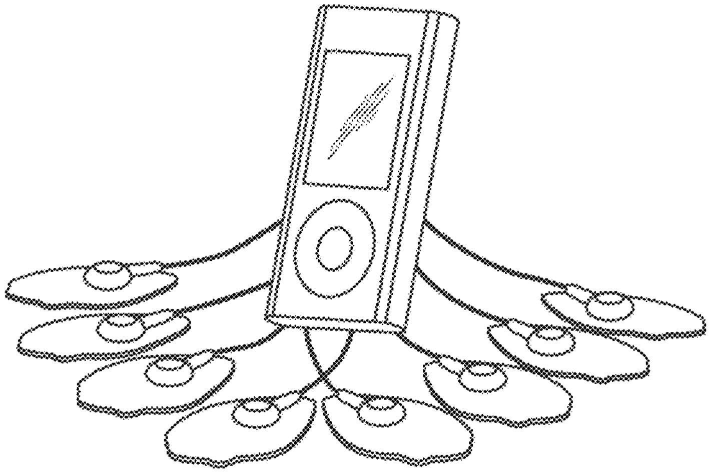
FIG. 1 depicts a programmed bioelectric stimulator for delivery to a subject connected to multiple soft conductive electrode pads.
Figure 2:
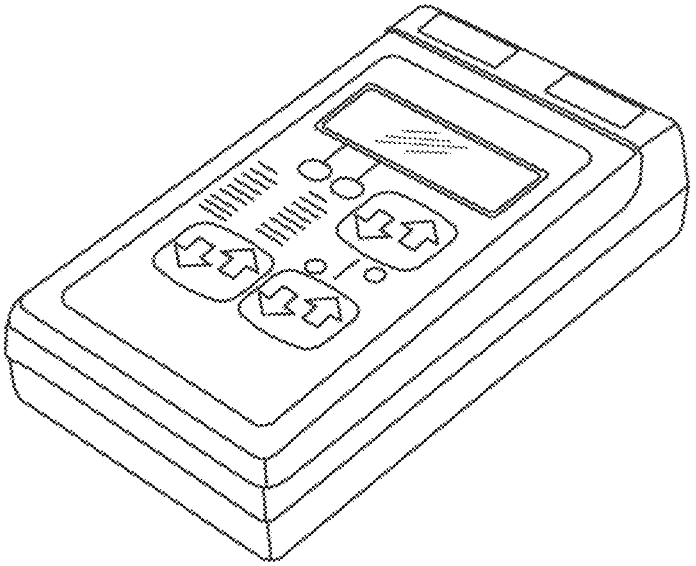
FIG. 2 depicts a programmed bioelectric stimulator as described herein.
Figure 3:
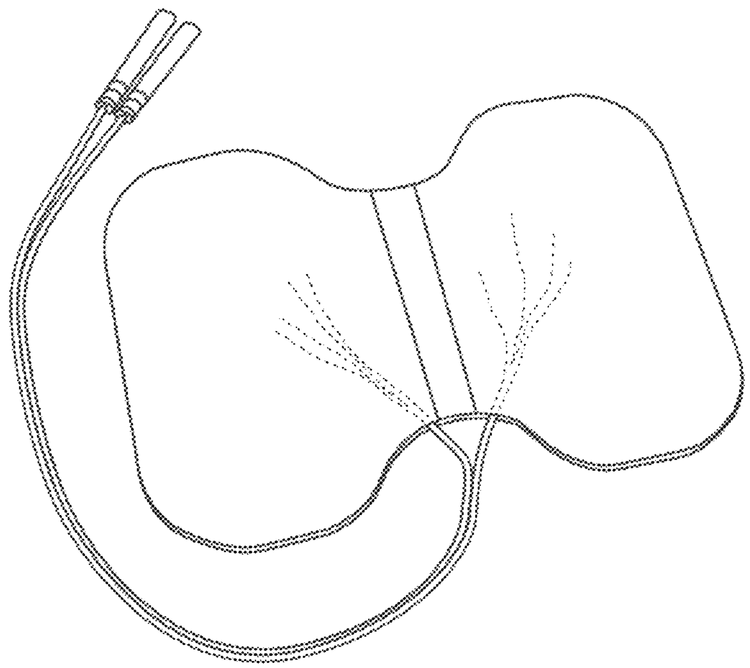
FIG. 3 depicts a conductive soft wrap which may be used with the described system.
Figure 4:
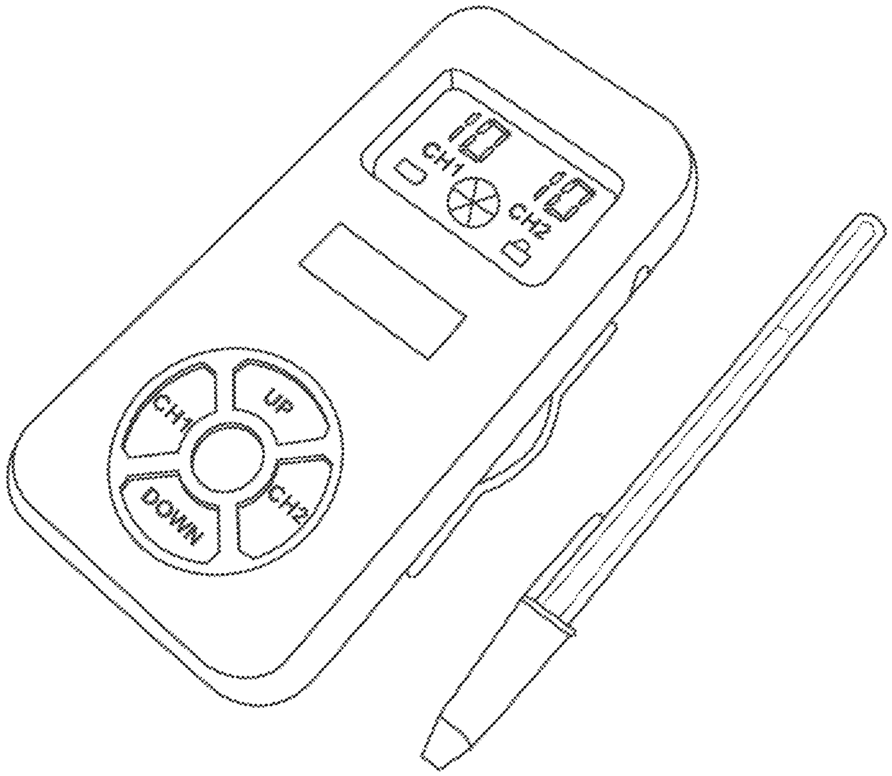
FIG. 4 depicts a programmed bioelectric stimulator depicted alongside a pen.

Referring now to FIG. 1, depicted is a stimulator for use in treating a human. The depicted device is about the size of a pen (FIG. 4) and is programmable.

A micro voltage signal generator for use herein may be produced utilizing the same techniques to produce a standard heart pacemaker well known to a person of ordinary skill in the art. An exemplary microvoltage generator is available from Mettler Electronics Corp. of Anaheim, California, US or HTM Electronica of Amparo, BR. The leading pacemaker manufacturers are Medtronic, Boston Scientific Guidant, Abbott St. Jude, BioTronik and Sorin Biomedica.

Construction of the electric signal generators and pacemakers is known in the art and can be obtained from OEM suppliers as well as their accompanying chargers and programmers. The electric signal generators are programmed to produce specific bioelectric signals to lead to specific protein expressions at precisely the right time for, e.g., optimal treatment or for tissue regeneration.

The biostimulator of FIG. 1 is depicted with multiple soft conductive electrode pads. Electrodes may be used to deliver a bioelectric signal to the subject by applying the electrodes to the subject's skin (e.g., on the skin above the thigh muscles or on the skin above the kidneys). In certain embodiments, a bioelectric stimulator is in electrical connection with a conductive soft wrap.

A bench top stimulator (e.g., a Mettler Model 240 Stimulator from Mettler Electronics of Anaheim, CA, US) may be pre-programmed with the bioelectric signaling sequence(s) for controlling the expression and/or release of SIRT.

In some embodiments, the application of bioelectric signals can further be used to modulate (e.g., upregulate) expression by the subject's cells the production of other biological molecules in addition to SIRT. See, e.g., U.S. Pat. No. 10,960,206 to Leonhardt et al. (Mar. 30, 2021) for "Bioelectric Stimulator," the contents of which are incorporated herein by this reference.

For example, in certain embodiments (e.g., in order to provide antiaging effects, cognitive improvements, sexual health, and/or cardiovascular protection), further specific bioelectric signals are applied that upregulate expression of sirtuins, klotho, and follistatin.

Further, in certain embodiments, bioelectric controlled modulating (e.g., upregulating) expression of the sirtuin family of proteins is added to bioelectric signals for modulating expression and/or release of klotho, follistatin, tropoelastin, stromal cell-derived factor-1 ("SDF1") (a stem cell recruiting signal), platelet-derived growth factor ("PDGF"), and/or insulin-like growth factor 1 ("IGF-1") for use, for example, in anti-aging therapy and muscle atrophy recovery. See, the incorporated U.S. Pat. No. 10,960,206 to Leonhardt et al.

The treatment and/or prevention of depression may involve the application of further bioelectric signal(s) to upregulate expression of Klotho. See, e.g., U.S. Patent Application Publication US 2020-0289826-A1 to Leonhardt et al. (Sep. 17, 2020) for "Klotho Modulation" and U.S. Patent Application Publication US 20210402184-A1 to Leonhardt et al. (Dec. 31, 2021) for "Klotho Modulation."

An implantable medical lead is described in U.S. Pat. No. 8,442,653 to Gill (May 14, 2013) for "Brain Electrode," the contents of which are incorporated herein by this reference.

In, for example, FIG. 15 of the incorporated U.S. Pat. No. 10,960,206 to Leonhardt et al., depicts an image of the signal (voltage and frequency) associated with stem cell proliferation: 2.5-6.0 V (4V depicted there), 20 Hz, pulse width 200-700 μsec, square wave. No special effects are attributed to a pulse width of 400 μsec, and sirtuin is not mentioned. The voltages described therein are also greater than those that would be associated with the microamperage utilized herein for upregulating expression of SIRT (as measured at the level of the stimulated cells).

Both wireless non-invasive and/or implantable wire lead ("electrode") based means may be used to deliver the regeneration and healing promoting bioelectric signal(s) to target organs such as the brain.

A wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970's for recharging externally implantable pacemakers.

Bioelectric stimulation can be done with the described bioelectric stimulator, which can have a pacing infusion lead with, e.g., a corkscrew lead placed/attached at, e.g., the center of the tissue to be stimulated and/or treated.

The bioelectric stimulator is actuated and runs through programmed signals to signal the release of, e.g., SIRT. In such a method, the electrical signal may be measured three (3) mm deep into the tissue.

Relationship Between the Components:

The micro voltage signal generator is attached to the pacing infusion lead with, e.g., a brain electrode (Medtronic) (e.g., for bioelectric stimulation of the brain), or conductive polymer bandage or patch to the tissue or organ to be treated. An external signal programmer may be used to program the micro voltage signal generator with the proper signals for treatment including the SIRT producing signal(s). The device battery may be re-chargeable with an external battery charging wand.

The essential elements are the micro voltage signal generator and the means for delivering the signal to the target tissue.

The signal generator may be external or internal. The transmission of the signal may be wireless, via liquid and/or via wires.

The tissue contact interface may be, e.g., a patch or bandage or may be via electrodes or leads. FDA cleared gel tape electrodes (Mettler) may be used for skin delivery. Electro acupuncture needles may be used to ensure the signals positively reach target tissues under the skin.

In certain preferred embodiments a method of stimulating the expression of SIRT in a living cell having a gene encoding a SIRT is described, wherein the method comprises: applying to the cell a bioelectric signal of, within 15%, 20 Hz at, within 15%, 400 μsec pulse width duration, wherein the amount of SIRT expression enhanced by this bioelectric signal is greater than that seen with a generic bioelectric cell stimulation alone as may be determined by an analysis of the upregulation of mRNA level/GAPDH fold gene expression in the cell in each situation.

Sirtuins activity in treating disease states and conditions is many-fold.

SIRT6's activity in treating and/or preventing depression relates to the suggestion that hippocampal SIRT6 contributes to the performance of depression-like behaviors by suppressing AKT/CRMP2 signaling, and FA ameliorates CUS-induced depression-like behaviors in mice as a potential pharmacologic inhibitor of SIRT6. Li et al., "Downregulation of hippocampal SIRT6 activates AKT/CRMP2 signaling and ameliorates chronic stress-induced depression-like behavior in mice," *Acta Pharmacol. Sin.* 2020 December; 41(12):1557-1567.

SIRT6's activity in treating and/or preventing metabolic stress was shown by Kanfi et al. The authors explored the role of SIRT6 in metabolic stress, wild type and transgenic (TG) mice overexpressing SIRT6 were fed a high fat diet. In comparison to their wild-type littermates, SIRT6 TG mice accumulated significantly less visceral fat, LDL-cholesterol, and triglycerides. TG mice displayed enhanced glucose tolerance along with increased glucose-stimulated insulin secretion. Gene expression analysis of adipose tissue revealed that the positive effect of SIRT6 overexpression is associated with down regulation of a selective set of peroxisome proliferator-activated receptor-responsive genes, and genes associated with lipid storage, such as angiopoietin-like protein 4, adipocyte fatty acid-binding protein, and diacylglycerol acyltransferase 1, which were suggested as potential targets for drugs to control metabolic syndrome. These results demonstrate a protective role for SIRT6 against the metabolic consequences of diet-induced obesity and suggest a potentially beneficial effect of SIRT6 activation on age-related metabolic diseases. Kanfi et al., "SIRT6 protects against pathological damage caused by diet-induced obesity," *Aging Cell,* 2010 April; 9(2):162-73.

Further data indicate that moderate, physiological overexpression of SIRT6 enhances insulin sensitivity in skeletal muscle and liver, engendering protective actions against diet-induced type 2 diabetes mellitus ("T2DM"). Hence, the present study provides support for the anti-T2DM effect of SIRT6 and suggests SIRT6 as a putative molecular target for anti-T2DM treatment. Anderson et al., "Enhanced insulin sensitivity in skeletal muscle and liver by physiological overexpression of SIRT6," *Mol. Metab.* 2015 Sep. 25; 4(11):846-56.

Aging leads to a gradual decline in physical activity and disrupted energy homeostasis. The NAD+-dependent SIRT6 deacylase regulates aging and metabolism through mechanisms that largely remain unknown. Roichman et al. showed that SIRT6 overexpression leads to a reduction in frailty and lifespan extension in both male and female B6 mice. A combination of physiological assays, in vivo multiomics analyses and 13C lactate tracing identified an age-dependent decline in glucose homeostasis and hepatic glucose output in wild type mice. In contrast, aged SIRT6-transgenic mice preserve hepatic glucose output and glucose homeostasis through an improvement in the utilization of two major gluconeogenic precursors, lactate and glycerol. To mediate these changes, mechanistically, SIRT6 increases hepatic gluconeogenic gene expression, de novo NAD+ synthesis, and systemically enhances glycerol release from adipose tissue. Roichman et al.'s findings show that SIRT6 optimizes energy homeostasis in old age to delay frailty and preserve healthy aging. Roichman et al., "Restoration of energy homeostasis by SIRT6 extends healthy lifespan," *Nat. Commun.* 2021 May 28; 12(1):3208.

SIRT6 deacetylase activity improves stress resistance via gene silencing and genome maintenance. Peng et al. revealed a deacetylase-independent function of SIRT6, which promotes anti-apoptotic gene expression via the transcription factor GATA4. SIRT6 recruits TIP60 acetyltransferase to acetylate GATA4 at K328/330, thus enhancing its chromatin binding capacity. In turn, GATA4 inhibits the deacetylase activity of SIRT6, thus ensuring the local chromatin accessibility via TIP60-promoted H3K9 acetylation. Significantly, the treatment of doxorubicin (DOX), an anticancer chemotherapeutic, impairs the SIRT6-TIP60-GATA4 trimeric complex, blocking GATA4 acetylation and causing cardiomyocyte apoptosis. While GATA4 hyperacetylation-mimic retains the protective effect against DOX, the hypoacetylation-mimic loses such ability. Thus, the data reveal a novel SIRT6-TIP60-GATA4 axis, which promotes the anti-apoptotic pathway to prevent DOX toxicity. Targeting the trimeric complex constitutes a new strategy to improve the safety of DOX chemotherapy in clinical application. Peng et al., "Deacetylase-independent function of SIRT6 couples GATA4 transcription factor and epigenetic activation against cardiomyocyte apoptosis," *Nucleic Acids Res.* 2020 May 21; 48(9):4992-5005.

SIRT6's activity in treating and/or preventing osteoporosis, oxidative stress plays a crucial role in osteoporosis. RES can reinforce resistance to oxidative damage and hence promote osteogenesis via the activation of SIRT1/FoxO1 signaling pathway, which provides a new idea for the prevention and treatment of osteoporosis. Jiang et al., "Resveratrol promotes osteogenesis via activating SIRT1/FoxO1 pathway in osteoporosis mice," *Life Sci.* 2020 Apr. 1; 246:117422.

With respect to osteopenia and osteoclast activation, the level of Sirt6 in human preosteoclasts was correlated positively with bone density and ERα but negatively with age. The results of Moon et al. suggest that deacetylation and upregulation of ERα by Sirt6 in preosteoclasts prevent bone loss by inhibiting osteoclast-mediated bone resorption. Activation of Sirt6 in preosteoclasts may provide a new therapeutic approach to attenuate osteoporosis in older or postmenopausal patients. Moon et al., "Sirtuin 6 in preosteoclasts suppresses age- and estrogen deficiency-related bone loss by stabilizing estrogen receptor α," *Cell Death Differ.* 2019 November; 26(11):2358-2370.

Deficiency of Sirtuin 6 (SIRT6), a chromatin-related deacetylase, in mice reveals severe premature aging phenotypes including osteopenia. However, the underlying molecular mechanisms of SIRT6 in bone metabolism are unknown. SIRT6 deficiency in mice produces low-turnover osteopenia caused by impaired bone formation and bone resorption, which are mechanisms similar to those of age-related bone loss. Mechanistically, SIRT6 interacts with runt-related transcription factor 2 (Runx2) and osterix (Osx), which are the two key transcriptional regulators of osteoblastogenesis, and deacetylates histone H3 at Ly sine 9 (H3K9) at their promoters. Hence, excessively elevated Runx2 and Osx in SIRT6(−/−) osteoblasts lead to impaired osteoblastogenesis. In addition, SIRT6 deficiency produces hyperacetylation of H3K9 in the promoter of dickkopf-related protein 1 (Dkk1), a potent negative regulator of osteoblastogenesis, and osteoprotegerin, an inhibitor of osteoclastogenesis. Therefore, the resulting up-regulation of Dkk1 and osteoprotegerin levels contribute to impaired bone remodeling, leading to osteopenia with a low bone turnover in SIRT6-deficient mice. These results establish a new link between SIRT6 and bone remodeling that positively regulates osteoblastogenesis and osteoclastogenesis.

The effects of SIRT6 on bone resorption remain controversial, with only one report of impaired osteoclast function. Sugatani et al., "SIRT6 deficiency culminates in low-turnover osteopenia," *Bone,* 2015 December; 81: 168-177.

To determine whether SIRT6 directly regulates bone metabolism, primary bone marrow stromal cells were cultured by Zhang et al. for osteogenesis and osteoclastogenesis separately to avoid indirect interference in vivo responses such as inflammation. Taken together, these results show that SIRT6 can directly regulate osteoblast proliferation and differentiation, resulting in attenuation in mineralization. Furthermore, SIRT6 can directly regulate osteoclast differentiation and results in a higher number of small osteoclasts, which may be related to overactive bone resorption. Zhang et al., "Phenotypic research on senile osteoporosis caused by SIRT6 deficiency," *Int. J. Oral Sci.* 2016 Jun. 30; 8(2):84-92.

Adult bone homeostasis requires a fine-tuned balance between the activity of osteoblasts and osteoclasts. This osteoblast-osteoclast coupling is therapeutically important because it limits the efficacy of most anabolic or anti-resorptive treatments for osteoporosis. Sirtuin6 (SIRT6), a histone deacetylase, was implicated recently as an important regulator in bone homeostasis, but its in vivo function in osteoblast lineage cells remains unclear, mainly due to a lack of in vivo experiments with osteoblast lineage specific Sirt6 knockout mice. Kim et al. showed that Sirt6 in mature osteoblasts and/or osteocytes inhibits osteoclastogenesis via a paracrine mechanism. Kim et al. found that osteoblast/osteocyte-specific Sirt6 knockout mice show reduced bone mass due to increased osteoclast formation. Mechanistically, Kim et al. attributed this increased osteoclastogenesis to decreased osteoprotegerin expression in Sirt6-null osteoblasts and osteocytes. This loss of Sirt6 in osteoblasts and osteocytes does not, however, alter bone formation parameters in vivo. It does accelerate osteogenic differentiation in ex vivo culture, indicating that the osteoblast/osteocyte-autonomous functions of SIRT6 have minor effects on the osteopenic phenotype. These results establish a critical role for SIRT6 in mature osteoblasts and osteocytes in adult bone homeostasis as a negative paracrine regulator of osteoclastogenesis. Kim et al., "Loss of Sirtuin 6 in osteoblast lineage cells activates osteoclasts, resulting in osteopenia," *Bone,* 2020 September; 138:115497.

SIRT6's activity in treating spinal cord injury relates to the observation that the upregulation of SIRT6 alleviated inflammation and oxidative stress and inhibited cell apoptosis in spinal cord injury. The findings indicated that SIRT6 attenuated spinal cord injury by suppressing inflammation, oxidative stress, and cell apoptosis. SIRT6 may represent a protective effect against spinal cord injury. C. Zhaohui and W. Shuihua, "Protective Effects of SIRT6 Against Inflammation, Oxidative Stress, and Cell Apoptosis in Spinal Cord Injury," *Inflammation,* 2020 October; 43(5):1751-1758.

With respect to aiding cardiac and other muscle, impaired autophagic flux induces aging-related ischemia vulnerability, which is a pathology related to cardiac aging. Li et al. confirmed that the accumulation of charged multivesicular body protein 2B (CHMP2B), a subunit of the ESCRT-III complex, in the heart can impair autophagy flux. However, whether CHMP2B accumulation contributes to aging-related intolerance to ischemia/reperfusion (UR) injury and the regulatory mechanism for CHMP2B in aged heart remain elusive. The cardiac CHMP2B level was significantly higher in aged human myocardium than that in young myocardium. Increased CHMP2B were shown to inhibit autophagic flux leading to the deterioration of MI/R injury in aged mice hearts. Interestingly, a negative correlation was observed between SIRT6 and CHMP2B expression in human heart samples. Specific activation of SIRT6 suppressed CHMP2B accumulation and ameliorated autophagy flux in aged hearts. Using myocardial-specific SIRT6 heterozygous knockout mice and recovery experiments confirmed that SIRT6 regulated myocardial CHMP2B levels. Finally, activation of SIRT6 decreased acetylation of Fox01 to promote its transcriptional function on Atrogin-1, a muscle-specific ubiquitin ligase, which subsequently enhanced the degradation of CHMP2B by Atrogin-1. SIRT6 may be used against aging-related myocardial ischemia vulnerability, particularly by preventing excessive accumulation of autophagy key factors. Li et al., "SIRT6 Protects Against Myocardial Ischemia-Reperfusion Injury by Attenuating Aging-Related CHMP2B Accumulation," *J. Cardio-*

*vasc. Transl. Res.* 2022 Mar. 2. doi: 10.1007/s12265-021-10184-y. Epub ahead of print. PMID: 35235147.

It has been demonstrated that Sirt6 and Sirt3 maintain each other's activity and protect the heart from developing diabetic cardiomyopathy. Kanwal et al., "The nuclear and mitochondrial sirtuins, Sirt6 and Sirt3, regulate each other's activity and protect the heart from developing obesity-mediated diabetic cardiomyopathy," *FASEB J.* 2019 October; 33(10):10872-10888. doi: 10.1096/fj.201900767R. Epub 2019 Jul. 12. Erratum in: FASEB J. 2020 October; 34(10):14057. PMID: 31318577; PMCID: PMC6766651.

Wang et al. obtained results suggesting that SIRT6 protects the heart from I/R injury through FoxO3α activation in the ischemic heart in an AMP/ATP-induced AMPK-dependent way, thus upregulating antioxidants and suppressing oxidative stress. Wang et al., "SIRT6 protects cardiomyocytes against ischemia/reperfusion injury by augmenting FoxO3α-dependent antioxidant defense mechanisms," *Basic Res. Cardiol.* 2016 March; 111(2):13.

Li et al. also separately demonstrated that SIRT6 prevented vascular calcification (VC) by suppressing the osteogenic transdifferentiation of VSMCs, and as such targeting SIRT6 may be an appealing therapeutic target for VC in chronic kidney disease. Li et al., "SIRT6 protects vascular smooth muscle cells from osteogenic transdifferentiation via Runx2 in chronic kidney disease," *J. Clin. Invest.* 2022 Jan. 4; 132(1):e150051.

Further, SIRT6 protein expression is reduced in human and mouse plaque Vascular Smooth Muscle Cells and is positively regulated by CHIP. SIRT6 regulates telomere maintenance and VSMC lifespan and inhibits atherogenesis, all dependent on its deacetylase activity. Grootaert et al. showed that endogenous SIRT6 deacetylase is an important and unrecognized inhibitor of VSMC senescence and atherosclerosis. Grootaert et al., "SIRT6 Protects Smooth Muscle Cells From Senescence and Reduces Atherosclerosis," *Circ. Res.* 2021 Feb. 19; 128(4):474-491.

Muscle wasting, also known as cachexia, is associated with many chronic diseases, which worsens prognosis of primary illness leading to enhanced mortality. Molecular basis of this metabolic syndrome is not yet completely understood. SIRT6 knockout (SIRT6-KO) mice display loss of muscle, fat and bone density, typical characteristics of cachexia. Samant et al. reported that SIRT6 depletion in cardiac as well as skeletal muscle cells promoted myostatin (Mstn) expression. They also observed upregulation of other factors implicated in muscle atrophy, such as angiotensin-II, activin, and Acvr2b, in SIRT6 depleted cells. SIRT6-KO mice showed degenerated skeletal muscle phenotype with significant fibrosis, an effect consistent with increased levels of Mstn. Additionally, Samant et al. observed that in an in vivo model of cancer cachexia, Mstn expression coupled with downregulation of SIRT6. Furthermore, SIRT6 overexpression downregulated the cytokine (TNFα-IFNγ)-induced Mstn expression in C2C12 cells and promoted myogenesis. From the ChIP assay, they found that SIRT6 controls Mstn expression by attenuating NF-κB binding to the Mstn promoter. Together, these data suggest a role for SIRT6 in maintaining muscle mass by controlling expression of atrophic factors like Mstn and activin. Samant et al., "The histone deacetylase SIRT6 blocks myostatin expression and development of muscle atrophy," *Sci. Rep.* 2017 Sep. 19; 7(1):11877.

Because of the mass and functions in metabolism, skeletal muscle is one of the major organs regulating whole body metabolic homeostasis. SIRT6, a histone deacetylase, has been shown to regulate metabolism in liver and brain; however, its specific role in skeletal muscle is undetermined. Cui et al. explored physiological function of SIRT6 in muscle. They generated a muscle-specific SIRT6 knockout mouse model. The mice with SIRT6 deficiency in muscle displayed impaired glucose homeostasis and insulin sensitivity, attenuated whole body energy expenditure, and weakened exercise performance. Mechanistically, deletion of SIRT6 in muscle decreased expression of genes involved in glucose and lipid uptake, fatty acid oxidation, and mitochondrial oxidative phosphorylation in muscle cells because of the reduced AMP-activated protein kinase (AMPK) activity. In contrast, overexpression of SIRT6 in C2C12 myotubes activates AMPK. Both gain- and loss-of-function experiments identify SIRT6 as a physiological regulator of muscle mitochondrial function. These findings indicate that SIRT6 is a potential therapeutic target for treatment of type 2 diabetes mellitus. Cui et al., "SIRT6 regulates metabolic homeostasis in skeletal muscle through activation of AMPK," *Am. J. Physiol. Endocrinol. Metab.* 2017 Oct. 1; 313(4):E493-E505.

With respect to treating and/or preventing erectile dysfunction, silent information regulator 2-related enzyme 1 (SIRT1) is an aging-related protein activated with aging. Yu et al. evaluated the role of SIRT1 in aging-related erectile dysfunction. The expression of SIRT1 was modulated in aged Sprague-Dawley rats following intragastric administration of resveratrol (Res; 5 mg kg−1), niacinamide (NAM; 500 mg kg−1) or Res (5 mg kg−1)+tadalafil (Tad; phosphodiesterase-5 [PDE5] inhibitor; 5 mg kg−1) for 8 weeks. Then, Yu et al. determined erectile function by the ratio of intracavernosal pressure (ICP)/mean systemic arterial pressure (MAP). Cavernosal tissues were extracted to evaluate histological changes, cell apoptosis, nitric oxide (NO)/cyclic guanosine monophosphate (cGMP), the superoxide dismutase (SOD)/3,4-methylenedioxyamphetamine (MDA) level, and the expression of SIRT1, p53, and forkhead box O3 (FOXO3a) using immunohistochemistry, terminal deoxynucleotidyl transferase (TdT)-mediated 2'-deoxyuridine 5'-triphosphate (dUTP) nick-end labeling (TUNEL), enzyme-linked immunosorbent assays, and western blot analysis. Compared with the control, Res treatment significantly improved erectile function, reflected by an increased content of smooth muscle and endothelium, NO/cGMP and SOD activity, and reduced cell apoptosis and MDA levels. The effect of Res was improved by adding Tad. In addition, the protein expression of SIRT1 was increased in the Res group, accompanied by decreased p53 and FOXO3a levels. In addition, inhibition of SIRT1 by NAM treatment resulted in adverse results compared with Res treatment. SIRT1 activation ameliorated aging-related erectile dysfunction, supporting the potential of SIRT1 as a target for erectile dysfunction treatment. Yu et al., "Modulation of SIRT1 expression improves erectile function in aged rats," Asian J. Androl. [Epub ahead of print].

In a different study, Yu et al. found that SIRT1 was expressed in cavernosal tissue, and it was downregulated in the corpora of diabetic rats. The administration of resveratrol upregulated the expression of SIRT1 and restored erectile function. In contrast, resveratrol downregulated the expression of p53 and FOXO3a, which regulate apoptosis and oxidative stress. Furthermore, the resveratrol-treated group showed an improvement in smooth muscle content, SOD activity and MDA levels when compared with the diabetic group. Therefore, the ability of resveratrol to improve diabetes-induced ED is likely related to its activation of SIRT1 expression, thus causing the suppression of apoptosis and resistance towards oxidative stress. Yu et al., "Resveratrol, an activator of SIRT1, restores erectile function in streptozotocin-induced diabetic rats," *Asian J. Androl.* 2013 September; 15(5):646-51.

The invention is further described by the following illustrative Examples.

EXAMPLES

Example I

Upregulation of SIRT Gene Expression

Figure 5:
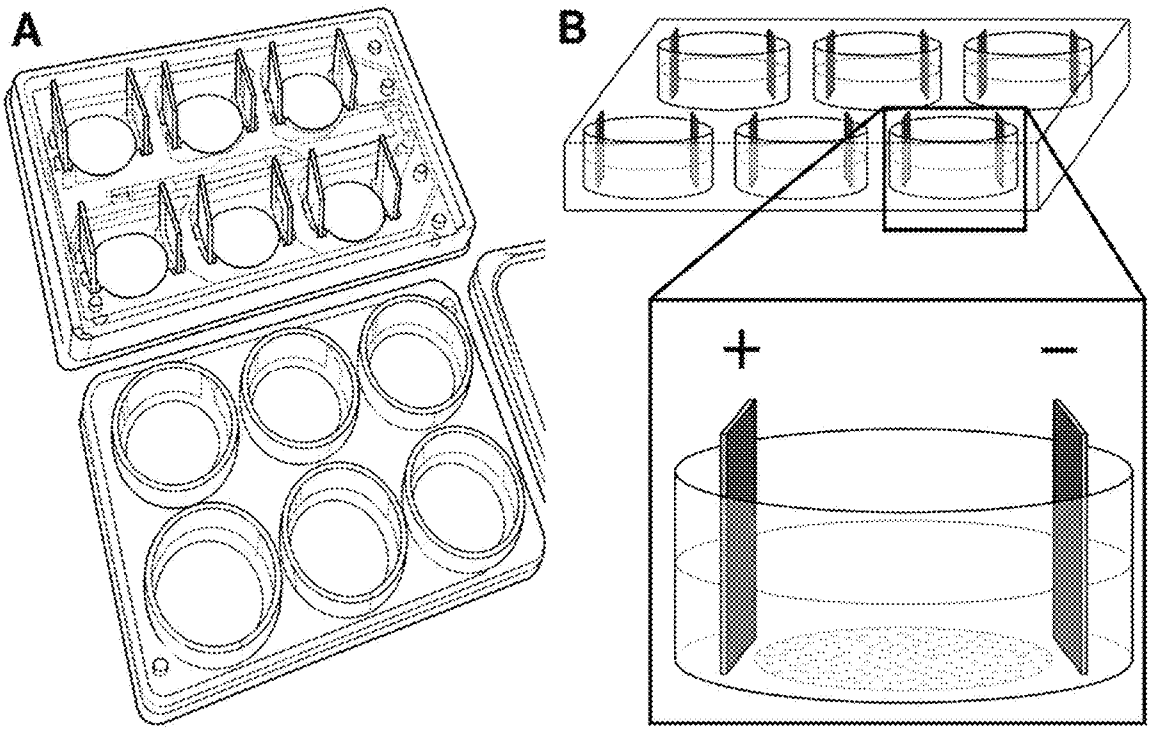
FIG. 5 depicts a bioelectric stimulation system for laboratory testing.

FIG. 5 depicts a bioelectric stimulation system. Cells and/or tissue are plated in each dish and cultured. Stimulation occurs using an electrode array (shown at the top of panel A), which is inverted and introduced into the 6-well dish where cells are grown. Each well receives uniform stimulation via a pair of carbon electrodes.

Various currents were applied to mammalian myoblast cells (C2C12 cells) including 50 μA and 500 μA. In each stimulation, 20 pps frequency (as expressed by Mettler electric signal generators) and 400 μs pulse duration for 30 or 60 minutes were applied to mouse myoblasts (progenitor skeletal muscle cells).

Figure 6:
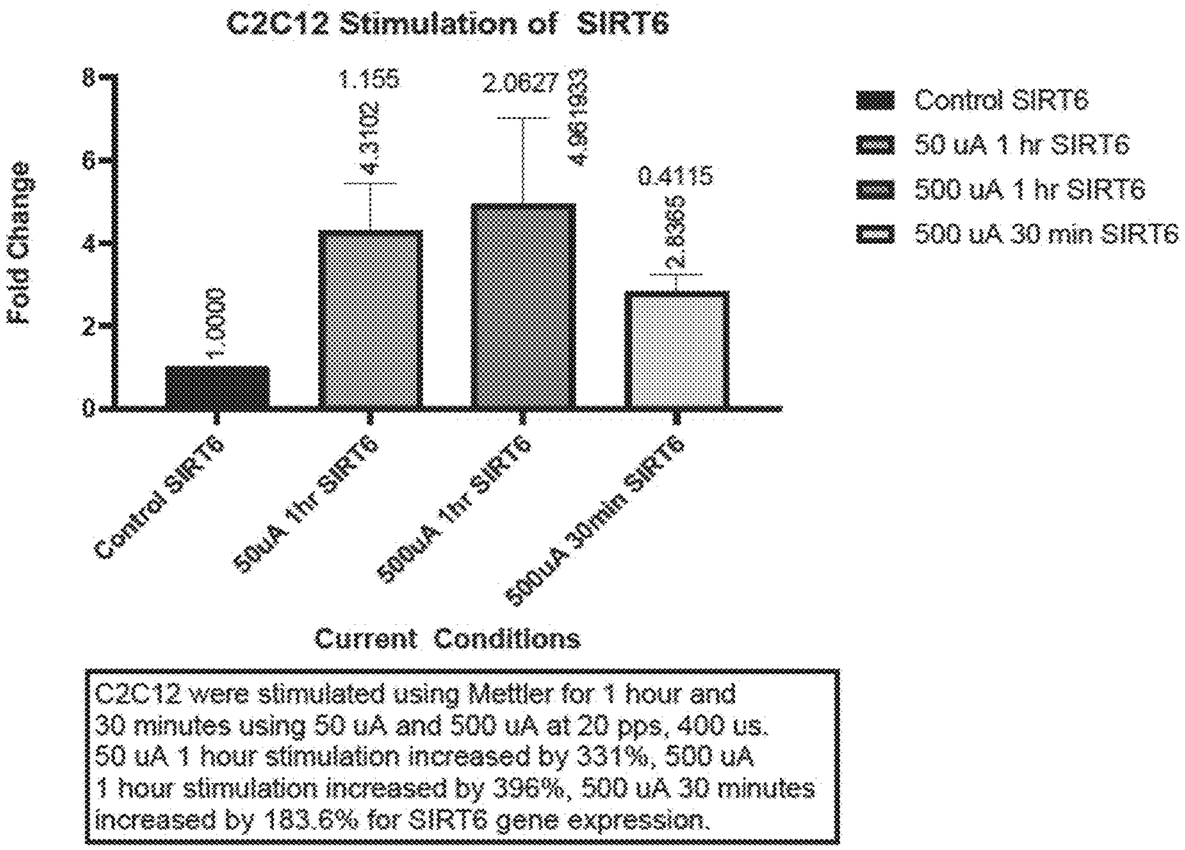
FIG. 6 is a graph depicting the results of the bioelectric stimulation of Example I on SIRT6 gene expression in myoblasts (C2C12 cells).

FIG. 6 graphically depicts the results of various bioelectric stimulations on SIRT6 gene expression in myoblasts.

Applying a bioelectric signal of 50 μA, 20 pps, 400 μs pulse duration, to living myoblast cells for 30 minutes resulted in a 55% increase in Sirt-1 expression.

Applying a bioelectric signal of 500 μA, 20 pps, 400 μs pulse duration, to living myoblast cells for 30 minutes resulted in a 55% increase in Sirt-1 expression.

A bioelectric signal of 50 μA, 20 pps, 400 μs pulse duration, applied for one-hour upregulated Sirt6 expression by 331%.

A bioelectric signal of 500 μA, 20 pps, 400 μs pulse duration, applied for 30 minutes upregulated Sirt6 expression 183.6%.

A bioelectric signal of 500 μA, 20 pps, 400 μs pulse duration, applied for one-hour upregulated Sirt6 expression 396%.

This finding in the C2C12 cell line is particularly relevant in view of Sirt6's profound beneficial effects on skeletal, smooth, and cardiac muscle.

Example II

Downregulation of SIRT Gene Expression

The expression of Sirtuin 1 and Sirtuin 6 is inhibited by currents of 1 mA or greater.

A bioelectric signal of 1 mA, 20 pps, 400 μs pulse duration, applied to the myoblast cells inhibited and Sirt1 and Sirt6 expression (data not shown).

Specifically, a bioelectric signal of 5 mA, 20 pps, 400 μs pulse duration, applied to the myoblast cells for one-hour downregulated Sirt1 expression by 27%.

A bioelectric signal of 5 mA, 20 pps, 400 μs pulse duration, applied to the myoblast cells for one-hour downregulated Sirt6 expression by 38.86%.

A bioelectric signal of 5 mA, 20 pps, 400 μs pulse duration, applied to the myoblast cells for 30 minutes downregulated Sirt6 expression by 65%.

REFERENCES (The contents of the entirety of each of which is incorporated herein by this reference.)

Anderson et al., "Enhanced insulin sensitivity in skeletal muscle and liver by physiological overexpression of SIRT6," *Mol. Metab.* 2015 Sep. 25; 4(11):846-56. doi: 10.1016/j.molmet.2015.09.003. PMID: 26629408; PMCID: PMC4632175.

Baohua Y., Li L., "Effects of SIRT6 silencing on collagen metabolism in human dermal fibroblasts," *Cell Biol. Int.* 2012 January; 36(1):105-8. doi: 10.1042/CBI20110268. PMID: 21981042.

Chen et al., "Sirt6 overexpression suppresses senescence and apoptosis of nucleus pulposus cells by inducing autophagy in a model of intervertebral disc degeneration," *Cell Death Dis.* 2018 Jan. 19; 9(2):56. doi: 10.1038/s41419-017-0085-5. PMID: 29352194; PMCID: PMC5833741.

Chen et al., "The role of Sirt6 in osteoarthritis and its effect on macrophage polarization," *Bioengineered.* 2022 April; 13(4):9677-9689. doi: 10.1080/21655979.2022.2059610. PMID: 35443857; PMCID: PMC9161952.

Cui et al., "SIRT6 regulates metabolic homeostasis in skeletal muscle through activation of AMPK," *Am. J. Physiol. Endocrinol. Metab.* 2017 Oct. 1; 313(4):E493-E505. doi: 10.1152/ajpendo.00122.2017. Epub 2017 Aug. 1. PMID: 28765271.

Garcia-Peterson et al., "SIRT6 histone deacetylase functions as a potential oncogene in human melanoma," *Genes Cancer.* 2017 September; 8(9-10):701-712. doi: 10.18632/genesandcancer.153. PMID: 29234488; PMCID: PMC5724804.

Garcia-Peterson et al., "The sirtuin 6: An overture in skin cancer," *Exp. Dermatol.* 2020 February; 29(2):124-135. doi: 10.1111/exd.14057. Epub 2019 December 29. PMID: 31696978; PMCID: PMC8205187.

Garth E., "Longevity Sirtuin Clinical Trial Teases Promising Results," *Longevity. Technology News* (Aug. 3, 2022).

Grabowska et al., "Sirtuins, a promising target in slowing down the ageing process," *Biogerontology,* 2017; 18(4): 447-476 (published online 2017 Mar. 3); doi: 10.1007/s10522-017-9685-9.

Grootaert et al., "SIRT6 Protects Smooth Muscle Cells From Senescence and Reduces Atherosclerosis," *Circ. Res.* 2021 Feb. 19; 128(4):474-491. doi: 10.1161/CIRCRESAHA.120.318353. Epub 2020 Dec. 22. Erratum in: *Circ. Res.* 2021 May 28; 128(11):e124. PMID: 33353368; PMCID: PMC7899748.

Harlan et al., "Enhanced SIRT6 activity abrogates the neurotoxic phenotype of astrocytes expressing ALS-linked mutant SOD1," *FASEB J.* 2019 June; 33(6):7084-7091. doi: 10.1096/fj.201802752R. Epub 2019 Mar. 6. PMID: 30841754; PMCID: PMC6529338.

Ji et al., "Overexpression of Sirt6 promotes M2 macrophage transformation, alleviating renal injury in diabetic nephropathy," *Int. J. Oncol.* 2019 July; 55(1):103-115. doi: 10.3892/ijo.2019.4800. Epub 2019 May 14. PMID: 31115579; PMCID: PMC6561622.

Jiang et al., "Resveratrol promotes osteogenesis via activating SIRT1/Fox01 pathway in osteoporosis mice," *Life Sci.* 2020 Apr. 1; 246:117422. doi: 10.1016/j.lfs.2020.117422. Epub 2020 Feb. 11. PMID: 32057903.

Jiang et al., "MDL-800, the SIRT6 Activator, Suppresses Inflammation via the NF-κB Pathway and Promotes Angiogenesis to Accelerate Cutaneous Wound Healing in Mice," *Oxid. Med. Cell Longev.* 2022 Apr. 27; 2022: 1619651. doi: 10.1155/2022/1619651. PMID: 35528512; PMCID: PMC9068290.

Kanfi et al., "SIRT6 protects against pathological damage caused by diet-induced obesity," *Aging Cell,* 2010 April;

9(2):162-73. doi: 10.1111/j.1474-9726.2009.00544.x. Epub 2009 Dec. 28. PMID: 20047575.

Kanfi et al., "The sirtuin SIRT6 regulates lifespan in male mice," *Nature.* 2012 Feb. 22; 483(7388):218-21. doi: 10.1038/nature10815. PMID: 22367546.

Kanwal et al., "The nuclear and mitochondrial sirtuins, Sirt6 and Sirt3, regulate each other's activity and protect the heart from developing obesity-mediated diabetic cardiomyopathy," *FASEB J.* 2019 October; 33(10):10872-10888. doi: 10.1096/fj.201900767R. Epub 2019 Jul. 12. Erratum in: *FASEB J.* 2020 October; 34(10):14057. PMID: 31318577; PMCID: PMC6766651.

Khan et al., "SIRT6 deacetylase transcriptionally regulates glucose metabolism in heart," *J. Cell. Physiol.* 2018 July; 233(7):5478-5489. doi: 10.1002/jcp.26434. Epub 2018 Feb. 22. Erratum in: *J. Cell. Physiol.* 2022 April; 237(4): 2288. PMID: 29319170.

Kim et al., "Loss of Sirtuin 6 in osteoblast lineage cells activates osteoclasts, resulting in osteopenia," *Bone,* 2020 September; 138:115497. doi: 10.1016/j.bone.2020.115497. Epub 2020 Jun. 27. PMID: 32599221.

Lappas M., "Anti-inflammatory properties of sirtuin 6 in human umbilical vein endothelial cells," *Mediators Inflamm.* 2012; 2012:597514. doi: 10.1155/2012/597514. Epub 2012 Oct. 24. PMID: 23132960; PMCID: PMC3486624.

Lee et al., "Overexpression of sirtuin 6 suppresses inflammatory responses and bone destruction in mice with collagen-induced arthritis," *Arthritis Rheum.* 2013 July; 65(7):1776-85. doi: 10.1002/a rt.37963. PMID: 23553536.

Lee et al., "Sirtuin signaling in cellular senescence and aging," *BMB Rep.* 2019 January; 52(1): 24-34 (published online 2019 Jan. 31); doi: 10.5483/BMBRep.2019.52.1.290.

Lee et al., "Sirtuin 6 deficiency induces endothelial cell senescence via downregulation of forkhead box M1 expression," *Aging* (Albany NY). 2020 Nov. 10; 12(21): 20946-20967. doi: 10.18632/aging.202176. Epub 2020 Nov. 10. PMID: 33171439; PMCID: PMC7695388.

Li et al., "Downregulation of hippocampal SIRT6 activates AKT/CRMP2 signaling and ameliorates chronic stress-induced depression-like behavior in mice," *Acta Pharmacol. Sin.* 2020 December; 41(12):1557-1567. doi: 10.1038/s41401-020-0387-5. Epub 2020 Apr. 7. PMID: 32265492; PMCID: PMC7921578.

Li et al., "SIRT6 protects vascular smooth muscle cells from osteogenic transdifferentiation via Runx2 in chronic kidney disease," *J. Clin. Invest.* 2022 Jan. 4; 132(1):e150051. doi: 10.1172/JC1150051. PMID: 34793336; PMCID: PMC8718147.

Li et al., "SIRT6 Protects Against Myocardial Ischemia-Reperfusion Injury by Attenuating Aging-Related CHMP2B Accumulation," *J. Cardiovasc. Transl. Res.* 2022 Mar. 2. doi: 10.1007/s12265-021-10184-y. Epub ahead of print. PMID: 35235147.

Li et al., "SIRT6 Widely Regulates Aging, Immunity, and Cancer," *Front Oncol.* 2022 Apr. 6; 12:861334. doi: 10.3389/fonc.2022.861334. PMID: 35463332; PMCID: PMC9019339.

Liao et al., "The Sirt6 gene: Does it play a role in tooth development?," *PLoS One.* 2017 Mar. 29; 12(3): e0174255. doi: 10.1371/journal.pone.0174255. PMID: 28355287; PMCID: PMC5371306.

Maszlag-Torok et al., "Gene variants and expression changes of SIRT1 and SIRT6 in peripheral blood are associated with Parkinson's disease," *Sci. Rep.* 2021 May 21; 11(1):10677. doi: 10.1038/s41598-021-90059-z. PMID: 34021216; PMCID: PMC8140123.

Moon et al., "Sirtuin 6 in preosteoclasts suppresses age- and estrogen deficiency-related bone loss by stabilizing estrogen receptor α," *Cell Death Differ.* 2019 November; 26(11):2358-2370. doi: 10.1038/s41418-019-0306-9. Epub 2019 Feb. 20. PMID: 30787391; PMCID: PMC6889517.

Mostoslaysky et al., "Genomic instability and aging-like phenotype in the absence of mammalian SIRT6," *Cell.* 2006 Jan. 27; 124(2):315-29. doi: 10.1016/j.cell.2005.11.044. PMID: 16439206.

Nicholatos et al., "Nicotine promotes neuron survival and partially protects from Parkinson's disease by suppressing SIRT6," *Acta Neuropathol. Commun.* 2018 Nov. 8; 6(1): 120. doi: 10.1186/s40478-018-0625-y. PMID: 30409187; PMCID: PMC6223043.

Okun et al., "Sirt6 alters adult hippocampal neurogenesis," *PLoS One.* 2017 Jun. 23; 12(6):e0179681. doi: 10.1371/journal.pone.0179681. PMID: 28644902; PMCID: PMC5482455.

Peng et al., "Deacetylase-independent function of SIRT6 couples GATA4 transcription factor and epigenetic activation against cardiomyocyte apoptosis," *Nucleic Acids Res.* 2020 May 21; 48(9):4992-5005. doi: 10.1093/nar/gkaa214. PMID: 32239217; PMCID: PMC7229816.

Pillai et al., "The nuclear sirtuin SIRT6 protects the heart from developing aging-associated myocyte senescence and cardiac hypertrophy," *Aging* (Albany NY). 2021 May 2; 13(9):12334-12358. doi: 10.18632/aging.203027. Epub 2021 May 2. PMID: 33934090; PMCID: PMC8148452.

Roichman et al., "Restoration of energy homeostasis by SIRT6 extends healthy lifespan," *Nat. Commun.* 2021 May 28; 12(1):3208. doi: 10.1038/s41467-021-23545-7. PMID: 34050173; PMCID: PMC8163764.

Samant et al., "The histone deacetylase SIRT6 blocks myostatin expression and development of muscle atrophy," *Sci. Rep.* 2017 Sep. 19; 7(1):11877. doi: 10.1038/s41598-017-10838-5. PMID: 28928419; PMCID: PMC5605688.

Shaikh et al., "Targeting anti-aging protein sirtuin (Sirt) in the diagnosis of idiopathic pulmonary fibrosis," *J. Cell. Biochem.* 2018 Nov. 2. doi: 10.1002/jcb.28033. PMID: 30390331.

Sugatani et al., "SIRT6 deficiency culminates in low-turnover osteopenia," *Bone,* 2015 December; 81: 168-177; doi: 10.1016/j.bone.2015.07.018. Epub 2015 Jul. 17. PMID: 26189760; PMCID: PMC4640951.

Sundaresan et al., "The sirtuin SIRT6 blocks IGF-Akt signaling and development of cardiac hypertrophy by targeting c-Jun," *Nat. Med.* 2012 November; 18(11):1643-50. doi: 10.1038/nm.2961. Epub 2012 Oct. 21. PMID: 23086477; PMCID: PMC4401084.

Tang et al., "Sirt6 in pro-opiomelanocortin neurons controls energy metabolism by modulating leptin signaling," *Mol. Metab.* 2020 July; 37:100994. doi: 10.1016/j.molmet.2020.100994. Epub 2020 Apr. 9. PMID: 32278654; PMCID: PMC7215198.

Thandavarayan et al., "Sirtuin-6 deficiency exacerbates diabetes-induced impairment of wound healing," *Exp. Dermatol.* 2015 October; 24(10):773-8. doi: 10.1111/exd.12762. Epub 2015 Aug. 18. PMID: 26010430; PMCID: PMC4583793.

Tian et al., "SIRT6 Is Responsible for More Efficient DNA Double-Strand Break Repair in Long-Lived Species,"

*Cell* Volume 177, Issue 3, P622-638.E22 (Apr. 18, 2019); DOI: doi.org/10.1016/j.ce11.2019.03.043.

Wang et al., "SIRT6 protects cardiomyocytes against ischemia/reperfusion injury by augmenting FoxO3α-dependent antioxidant defense mechanisms," *Basic Res. Cardiol.* 2016 March; 111(2):13. doi: 10.1007/s00395-016-0531-z. Epub 2016 Jan. 19. PMID: 26786260.

Xin et al., "Sirtuin 6 ameliorates alcohol-induced liver injury by reducing endoplasmic reticulum stress in mice," *Biochem. Biophys. Res. Commun.* 2021 Mar. 12; 544:44-51. doi: 10.1016/j.bbrc.2021.01.061. Epub 2021 Jan. 28. PMID: 33516881.

Xu et al., "SIRT6 rescues the age related decline in base excision repair in a PARP1-dependent manner," *Cell Cycle.* 2015; 14(2): 269-276; doi: 10.4161/15384101.2014.980641.

Yang et al., "SIRT6 protects vascular endothelial cells from angiotensin II-induced apoptosis and oxidative stress by promoting the activation of Nrf2/ARE signaling," *Eur. J. Pharmacol.* 2019 Sep. 15; 859:172516. doi: 10.1016/j.ejphar.2019.172516. Epub 2019 Jun. 29. PMID: 31265839.

Yang et al., "Roles of SIRT6 in kidney disease: a novel therapeutic target," *Cell. Mol. Life Sci.* 2021 Dec. 24; 79(1):53. doi: 10.1007/s00018-021-04061-9. PMID: 34950960.

Yu et al., "Resveratrol, an activator of SIRT1, restores erectile function in streptozotocin-induced diabetic rats," *Asian J. Androl.* 2013 September; 15(5):646-51.

Yu et al., "Modulation of SIRT1 expression improves erectile function in aged rats," *Asian J. Androl.* (Epub ahead of print 2022 Feb. 18). Available from: www.ajandrology.com/preprintarticle.asp?id=337880.

Zhang et al., "Phenotypic research on senile osteoporosis caused by SIRT6 deficiency," *Int. J. Oral Sci.* 2016 Jun. 30; 8(2):84-92. doi: 10.1038/ijos.2015.57. PMID: 27357320; PMCID: PMC4932771.

Zhang et al., "SIRT6 deficiency results in developmental retardation in cynomolgus monkeys," *Nature.* 2018 August; 560(7720):661-665. doi: 10.1038/s41586-018-0437-z. Epub 2018 Aug. 22. PMID: 30135584.

Zhang et al., "Sirt6 Alleviated Liver Fibrosis by Deacetylating Conserved Lysine 54 on Smad2 in Hepatic Stellate Cells," *Hepatology.* 2021 March; 73(3):1140-1157. doi: 10.1002/hep.31418. Epub 2020 Nov. 10. PMID: 32535965; PMCID: PMC8048913.

Zhaohui C., Shuihua W., "Protective Effects of SIRT6 Against Inflammation, Oxidative Stress, and Cell Apoptosis in Spinal Cord Injury," *Inflammation,* 2020 October; 43(5):1751-1758. doi: 10.1007/s10753-020-01249-2. PMID: 32445068.

Zhu et al., "SIRT6 controls hepatic lipogenesis by suppressing LXR, ChREBP, and SREBP1*," Biochim. Biophys. Acta Mol. Basis Dis.* 2021 Dec. 1; 1867(12):166249. doi: 10.1016/j.bbadis.2021.166249. Epub 2021 Aug. 21. PMID: 34425214; PMCID: PMC8488016.

Zou et al., "SIRT6 inhibition delays peripheral nerve recovery by suppressing migration, phagocytosis and M2-polarization of macrophages," *Cell. Biosci.* 2021 Dec. 14; 11(1):210. doi: 10.1186/s13578-021-00725-y. PMID: 34906231; PMCID: PMC8672560.

U.S. Pat. No. 8,442,653 to Gill (May 14, 2013) for "Brain Electrode."

U.S. Patent Application Publication US 2020-0289826-A1 to Leonhardt et al. (Sep. 17, 2020) for "Klotho Modulation."

U.S. Patent Application Publication US 2021-0402184-A1 to Leonhardt et al. (Dec. 31, 2021) for "Klotho Modulation."

U.S. Pat. No. 10,960,206 to Leonhardt et al. (Mar. 30, 2021) for "Bioelectric Stimulator."

What is claimed is:

1. A method of treating muscle atrophy in a subject, the method comprising:

applying to skeletal muscle tissue of the subject a bioelectric signal produced by a bioelectric stimulator comprising an electric signal generator and at least one electrode, wherein the bioelectric signal:

comprises a biphasic pulse, has a frequency within ±15% of 20 Hz, has a pulse width within ±15% of 400 microseconds (μsec), has a current of about 50 microamps (μA), and is administered for about one hour, thereby increasing expression of sirtuin 6 (SIRT6) in skeletal muscle cells and treating muscle atrophy in the subject.

2. The method of claim 1, wherein the bioelectric signal increases SIRT6 expression by about 331%.

3. The method of claim 1, wherein the bioelectric signal is administered transcutaneously.

4. The method of claim 1, wherein the bioelectric signal is administered via an implanted electrode positioned in skeletal muscle tissue.

5. The method of claim 1, wherein the muscle atrophy is age-related muscle degeneration.

6. The method of claim 1, wherein the method is performed to increase skeletal muscle mass for bodybuilding.

7. A method of treating muscle atrophy in a subject, the method comprising:

applying to skeletal muscle tissue of the subject a bioelectric signal produced by a bioelectric stimulator comprising an electric signal generator and at least one electrode, wherein the bioelectric signal:

comprises a biphasic pulse, has a frequency within ±15% of 20 Hz, has a pulse width within ±15% of 400 μsec, has a current of from about 50 μA to about 500 μA, and is administered for from about thirty (30) minutes to about one hour, thereby increasing expression of SIRT6 in skeletal muscle cells and treating muscle atrophy in the subject.

8. The method of claim 7, wherein:

application of 50 μA for one hour increases SIRT6 expression by about 331%.

9. The method of claim 7, wherein:

application of 500 μA for 30 minutes increases SIRT6 expression by about 183.6%.

10. The method of claim 7, wherein:

application of 500 μA for one hour increases SIRT6 expression by about 396%.

11. The method of claim 7, wherein the muscle atrophy comprises cachexia.

12. A method of modulating expression of sirtuin 6 (SIRT6) in skeletal muscle cells of a subject, the method comprising:

applying to skeletal muscle tissue of the subject a first bioelectric signal produced by a bioelectric stimulator comprising an electric signal generator and at least one electrode, wherein the first bioelectric signal:

comprises a biphasic pulse,
has a frequency within ±15% of 20 Hz,
has a pulse width within ±15% of 400 μsec,
has a current of less than 575 μA, and
is administered for at least thirty (30) minutes,
thereby increasing expression of SIRT6 in skeletal muscle cells,
and wherein applying a second bioelectric signal having the same frequency and pulse width but having a current of at least 1 milliamp (mA) inhibits expression of SIRT6 in skeletal muscle cells.

13. The method of claim 12, wherein the first bioelectric signal has a current of about 50 μA.

14. The method of claim 12, wherein the second bioelectric signal has a current of about 5 mA.

15. The method of claim 12, wherein the first and second bioelectric signals differ only in current amplitude.

16. The method of claim 12, further comprising treating muscle atrophy in the subject by applying the first bioelectric signal.

* * * * *